United States Patent

Kaiping et al.

[11] Patent Number: 5,234,553
[45] Date of Patent: Aug. 10, 1993

[54] PROCESS FOR OBTAINING A PURE HYDROCARBON FROM A SUMP PRODUCT OF AN EXTRACTIVE DISTILLATION

[75] Inventors: Martin Kaiping, Essen; Udo Klaumunzner, Mulheim/Ruhr; Hans-Christoph Schneider, Hattingen/Ruhr; Hans-Jurgen Vollmer, Essen, all of Fed. Rep. of Germany

[73] Assignee: Krupp Koppers GmbH, Essen, Fed. Rep. of Germany

[21] Appl. No.: 918,262

[22] Filed: Jul. 22, 1992

[30] Foreign Application Priority Data

Sep. 25, 1991 [DE] Fed. Rep. of Germany ....... 4131938

[51] Int. Cl.$^5$ .............................. B01D 3/40; C07C 7/08
[52] U.S. Cl. ........................................ 203/58; 203/78; 203/84; 202/154; 585/808; 585/860; 585/865
[58] Field of Search .................. 203/58, 88, 78, 84; 208/313, 354, 355, 358, 361, 352; 585/808, 860, 862, 865; 202/153, 154

[56] References Cited

U.S. PATENT DOCUMENTS

| | | | |
|---|---|---|---|
| 3,232,850 | 2/1966 | Renberg et al. | 208/313 |
| 4,201,633 | 5/1980 | Paret et al. | 585/808 |
| 4,664,783 | 5/1987 | Preusser et al. | 208/313 |
| 4,776,927 | 10/1988 | Emmrich et al. | 203/DIG. 9 |

Primary Examiner—Wilbur Bascomb, Jr.
Attorney, Agent, or Firm—Michael J. Striker

[57] ABSTRACT

Process for obtaining a pure hydrocarbon from a starting material containing the hydrocarbon including performing an extractive distillation of the starting material containing the hydrocarbon in an extractive distillation column using a solvent comprising an N-substituted morpholine having substituents with no more than seven carbon atoms; feeding the sump product of the extractive distillation column into a distillation separator column at an entry point in a center portion of the distillation separator column; distilling off the hydrocarbon from the top of the distillation separator column but advantageously returning a minor portion of it as a reflux; drawing off solvent from the sump of the distillation separator column; feeding the solvent drawn off from the sump of the distillation separator column into an evaporator to form a vapor in the evaporator at the pressure, $p_2$, the pressure $p_2$ in the evaporator being lower than the pressure $p_1$ in the sump of the distillation separator column; condensing the vapor formed in the evaporator to form a condensate, feeding the condensate back to the distillation separator column and drawing off solvent as a liquid solvent from the sump of the evaporator and feeding back the liquid solvent to the extractive distillation column.

4 Claims, 1 Drawing Sheet

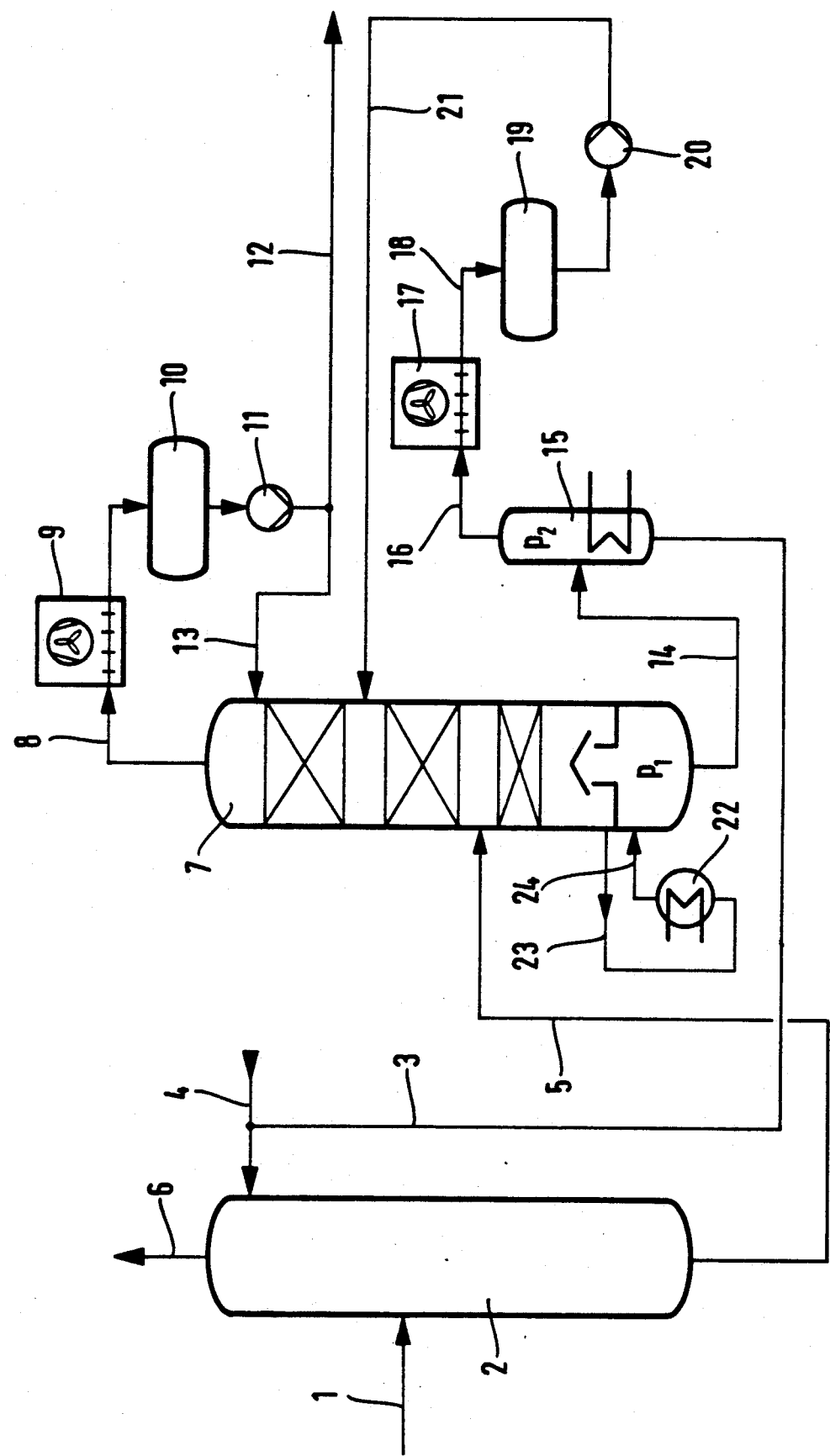

PROCESS FOR OBTAINING A PURE HYDROCARBON FROM A SUMP PRODUCT OF AN EXTRACTIVE DISTILLATION

BACKGROUND OF THE INVENTION

The present invention relates to a process or method for obtaining a pure hydrocarbon from a sump product of an extractive distillation.

An extractive distillation using an N-substituted morpholine, whose substituents do not contain more than seven carbon atoms, as selective solvent is known, in which the sump product is fed into a center portion of a distillation separator column. The hydrocarbon materials are distilled off the top of the distillation separator column, while the solvent is drawn off from the sump of the distillation separator column and after an appropriate cooling is returned to the extractive distillation column.

Extractive distillation of hydrocarbon-containing starting materials using the above-mentioned N-substituted morpholine, particularly N-formyl morpholine, as selective solvent, has been known for a long time and is currently used as a large-scale industrial process for obtaining highly pure aromatic hydrocarbons. The process has been used to obtain other types of hydrocarbon substances, e.g. olefins and diolefins. The major portion of the solvent in the sump of the extractive distillation column is enriched with the hydrocarbons obtained from the appropriate entry product and the hydrocarbons must be separated in a downstream distillation separator column. The hydrocarbons to be obtained are distilled off the top of the distillation separator column, while the solvent is obtained as a sump product and is fed back to the extractive distillation column. The distillation separator column has a side boiler for heating as well as the conventional sump boiler, which vaporizes the reflux coming from the distillation separator column.

In performing the above-described process one understandably tries to obtain as complete a separation of the hydrocarbons as possible from the solvent in the distillation separator column to obtain them with a minimum loss. In the currently practiced methods of this kind however this could only be achieved by operation of the sump at a temperature which was so high that high pressure steam was required for column heating, while for heating of the extractive distillation column normally low pressure steam was sufficient. An additional disadvantage of operation with comparatively high temperature in the separator column is that there is an increased tendency for thermal decomposition of the solvent because of the comparatively high temperature in the distillation separator column.

SUMMARY OF THE INVENTION

It is an object of the present invention to provide an improved process for separation of hydrocarbons from the sump product of an extractive distillation of the above-described type in which a good separation is obtained, while an operating temperature and heat content of the separator column are as low as possible so that distillation low pressure steam can be used for heating the distillation separator column.

This object and others which will be made more apparent hereinafter is attained in a process for separation of hydrocarbons from a sump product of an extractive distillation column of the above-described type.

According to the invention, the solvent drawn from the sump of the distillation separator column is fed to an evaporator, which is operated at a pressure $p_2$, which is lower than the pressure $p_1$ in the sump of the separator column. The vapor issuing from the evaporator condenses to form a condensate, the condensate is collected and is fed back into the distillation separator column, while the solvent in a liquid state is drawn from the sump of the evaporator and is returned to the extractive distillation column.

In the method of the invention the solvent drawn from the sump of the distillation separator column is subjected to a repeated partial vaporization at a lower pressure than exists in the sump of the distillation separator column, which results in a better separation of the hydrocarbons from the solvent. Since the solvent can be fed back with a higher purity into the extractive distillation column, the separation in the extractive distillation column is better or more complete. Simultaneously a lowering of the sump temperature in the distillation separator column is possible, because of the reduced pressure in the evaporator, so that the distillation separator column can be economically operated at a reduced pressure. Besides the desired cost saving, also the solvent has a reduced heat content. Advantageously the distillation separator column and the evaporator are operated at the same temperature.

In performing the process according to the invention the extent to which the pressure $p_2$ must be lowered relative to $p_1$ in the evaporator naturally depends on the hydrocarbons and the solvent used. In practice the process parameters must be varied so that the greatest reduction of the hydrocarbon content in the solvent at the same comparatively low sump temperature in the distillation separator column is achieved. Generally the value for $p_2$ is arbitrarily selected, but the value for $p_2$ must naturally be lower than that for $p_1$. In obtaining pure benzene using N-formylmorpholine (NFM) as selective solvent, for example, the value for $p_2$ can be between 0.15 and 0.077 bar, while the value for $p_1$ is around 0.368 bar.

An evaporator, a condenser, a collector or collection vessel and a pump are required for the method according to the invention. This additional apparatus expense is however largely compensated, because a second sump boiler and the standard side boiler on the distillation separator column can be eliminated.

BRIEF DESCRIPTION OF THE DRAWING

The objects, features and advantages of the present invention will now be illustrated in more detail by the following detailed description, reference being made to the accompanying drawing in which:

The sole FIGURE is a flow chart of a process for obtaining a pure hydrocarbon from the distillation separator column, although steps unnecessary for a basic understanding of the method including venting steps, heat exchangers, measurement and regulation steps and other steps have been omitted from the drawing for simplicity.

DETAILED DESCRIPTION OF THE PREFERRED EMBODIMENT

A starting material containing a hydrocarbon is fed through the pipe 1 into a central portion of an extractive distillation column 2. Since the extractive distillation column 2 is not the subject of the present invention, the individual features of the process occurring in it are not explained in detail here. The extractive distillation column can be a conventional distillation column with plates and other features. Fresh solvent is input to the extractive distillation column 2 through the connector pipe 4 connected to the top of the extractive distillation column 2. Solvent is also returned to the extractive distillation column 2 through the pipe 3 which is connected to the connector pipe 4. In the extractive distillation column 2 the solvent in the sump of the column is enriched with the hydrocarbon from the starting materials. The sump product is drawn off from the extractive distillation column 2 through pipe 5. At the same time the lower boiling components of the starting materials escape from the top of the extractive distillation column and are taken off through the pipe 6 for further processing. The sump product of the extractive distillation 2 is fed through the pipe 5 to the distillation column 7 and is conducted into a center portion of this column, which has plates or other structures.

In the distillation column 7 the pure hydrocarbon is distillatively separated from the solvent. These hydrocarbon are drawn off in vapor form from the top of this distillation separator column 7 and are conducted through the pipe 8 into the condenser 9, in which it condenses and arrives subsequently in the collector 10. The pure hydrocarbon is drawn from the collector 10 in a liquid state by the pump 11. The major portion of the pure hydrocarbon is delivered through pipe 12 for further processing while a minor portion is returned through pipe 13 as a reflux to the distillation separator column 7. The solvent already largely separated from the hydrocarbon materials can be drawn off from the sump of the distillation separator column 7 through the pipe 14. While in the prior art the solvent was fed back directly to the extractive distillation column after an appropriate cooling, in the method according to the invention the solvent is fed from the distillation separator column through the pipe 14 into evaporator 15, in which it experiences an additional partial vaporization. As has already been mentioned, the pressure $p_2$ in the evaporator 15 is lower than the pressure $p_1$ in the sump of the separator column 7. The vapor issuing from the evaporator 15, which consists predominantly of hydrocarbons released from the solvent, is drawn off through pipe 16 and arrives, after condensation in the condense 17, in the collector 19 through the pipe 18. From there the hydrocarbon is fed back in the liquid state through the pipe 21 by pump 20 to the distillation separator column 7. The feedback in this column occurs at an entry point advantageously between an entry point for the sump product from the extractive distillation column and an entry point for the reflux. The solvent, which now has a very high purity, is drawn off in the liquid state from the sump of the evaporator 15 and is fed back through the pipe 3 into the extractive distillation column 2. The solvent here experiences any necessary cooling prior to feedback. This can occur in a known way by indirect heat exchange with the other product flows of the process. Individual elements of this cooling are not shown in the flow chart in the drawing, since they are not part of the invention. At the bottom of the distillation separator column 7 the sump boiler 22 is located, which is connected by the pipes 23 and 24 with the distillation separator column 7, and in this case is sufficient for the heating requirements of this column. Because of the comparatively low temperature required in the method of the invention, low pressure steam can be used for heating the sump boiler 22. Additional sump and side boilers are normally not required for operation of the separator column 7. Because of the comparatively lower temperature in the distillation separator column 7 it is possible to adjust the top temperature in this column low enough so that an air cooling can be used in the condenser 9.

The efficiency of the method according to the invention is shown by the following example. The method of the invention is successful in obtaining pure benzene by extractive distillation with N-Formylmorpholine (NFM) as solvent, and this application is used to illustrate the method. The sump product drawn from the extractive distillation column 2 had the following composition:

| Benzene | 20 956 kg/h |
|---|---|
| NFM | 90 946 kg/h |
| Methyl cyclohexane | 3.25 kg/h |
| dimethyl cyclopentane | 1.997 kg/h |

This sump product was conducted into the separator column for separation of the benzene from the solvent (NFM). The results obtained in conventional operation without the additional evaporator are shown in the following Table 1.

TABLE 1

RESULTS OF THE CONVENTIONAL SEPARATION

|  | TEMP. °C. | PRESSURE, bar | Benzene Content in NFM, % |
|---|---|---|---|
| Sump Separator Column (conventional set up) | @ 195 | @ 0.55 | @ 1 |
|  | @ 185 | @ 0.37 | @ 0.55 |

In contrast table 2 shows the results for the method according to the invention with different pressures and temperatures in the additional evaporator:

TABLE 2

RESULTS FOR THE SEPARATION ACCORDING TO THE INVENTION

|  | TEMP, °C. | PRESSURE, bar | BENZENE CONTENT in NFM, % |
|---|---|---|---|
| Sump separator column before evaporator | 125 | 0.368 | 4.2 |
| NFM to ED | 125 | 0.15 | 1.4 |
| after evaporator | 125 | 0.077 | 0.5 |
| Sump separator column before evaporator | 140 | 0.368 | 2.8 |
| NFM to ED | 140 | 0.15 | 0.8 |
| after evaporator | 140 | 0.116 | 0.5 |

The results of the method of the invention as shown in Table 2 show that with the additional evaporator, which operates at a lower pressure than the separator column, an additional benzene separation is possible, since the benzene content is shown to be reduced to 0.5% in the solvent after the evaporator. A benzene content this low could only be obtained in the conventional process at higher temperature and lower pressure. In the method according to the invention a comparatively high benzene content in the sump product of the separator column is required by the lower operating temperature in this column. These lower operating temperatures allow however the heating of the separator column with economical low pressure steam. The comparatively high benzene content in the sump product of the separator column is not troublesome, because of the subsequent treatment of the sump product in the evaporator.

While the invention has been illustrated and described in method for obtaining a pure hydrocarbon from a sump product of an extractive distillation, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

We claim:

1. Process for obtaining a pure hydrocarbon from a starting material containing the hydrocarbon, said process comprising the steps of:
   a) performing an extractive distillation of a starting material containing a hydrocarbon in an extractive distillation column having a sump, said extractive distillation using a solvent comprising an N-substituent morpholine having substituents with no more than seven carbon atoms, to form a sump product;
   b) feeding the sump product from the sump of the extractive distillation column into a distillation separator column provided with a sump boiler, a top and a sump, said feeding being at an entry point in a center portion of the distillation separator column;
   c) distilling off the hydrocarbon from the top of the distillation separator column;
   d) drawing off solvent from the sump of the distillation separator column;
   e) feeding the solvent drawn off the sump of the distillation separator column into an evaporator to form a vapor in the evaporator, the pressure $p_2$ in the evaporator being lower than the pressure $p_1$ in the sump of the distillation separator column;
   f) condensing the vapor formed in the evaporator to form a condensate;
   g) feeding the condensate back to the distillation separator column; and
   h) drawing off solvent as a liquid solvent from the evaporator and feeding back the liquid solvent to the extractive distillation column.

2. Process as defined in claim 1, further comprising operating the distillation separator column and the evaporator at the same temperature.

3. Process as defined in claim 1, further comprising returning a minor portion of the hydrocarbon distilled off from the distillation separator column to the top of the distillation separator column as a reflux at an entry point of the distillation separator column and feeding the condensate to an entry point of the distillation separator column between the entry point for the reflux and the entry point for the sump product from the extractive distillation column.

4. Process as defined in claim 1, further comprising operating the distillation separator column at a temperature low enough to allow heating of the distillation separator column with low pressure steam.

* * * * *